United States Patent [19]

Mann

[11] 4,411,916

[45] Oct. 25, 1983

[54] METHOD OF PRODUCING MILK FACTOR

[75] Inventor: George V. Mann, Nashville, Tenn.

[73] Assignee: Vanderbilt University, Nashville, Tenn.

[21] Appl. No.: 390,309

[22] Filed: Jun. 21, 1982

Related U.S. Application Data

[63] Continuation-in-part of Ser. No. 209,835, Nov. 24, 1980, abandoned.

[51] Int. Cl.$^3$ .......................... A23C 9/12; C12P 1/04; C12R 1/39; A61K 35/00
[52] U.S. Cl. ........................................ 426/43; 426/61; 435/170; 435/876; 424/115
[58] Field of Search .................... 426/43, 34, 41, 42, 426/61; 435/170, 41, 253, 876; 424/115

[56] References Cited

PUBLICATIONS

Mann, G. V.; Milk Factor-A Regulator of Cholesteremia; *Abstract American Society of Clinical Nutrition*, May 3, 1979.

Mann, G. V.; Ein Regulator den Cholesteramie; *Bulletin European Organization for Control of Circulatory Disease*, Bonn; Nov. 9, 1979.

*Primary Examiner*—Raymond N. Jones
*Assistant Examiner*—Elizabeth J. Curtin

[57] ABSTRACT

The substance naturally present in milk (referred to as Milk Factor or MF) which is capable of inhibiting mammalian synthesis of cholesterol is produced by a fermentation process using a culture of *Pseudomonas fluorescens loitokitok* or other Milk Factor—producing strain of *P. fluorescens* in a culture medium containing glutaconic acid. The process may be used to increase the Milk Factor content of milk, yogurt, or similar dairy product, or the Milk Factor may be recovered from a culture medium and concentrated, crystallized and used as a food additive.

7 Claims, No Drawings

METHOD OF PRODUCING MILK FACTOR

CROSS-REFERENCE

This application is a continuation-in-part of copending application Ser. No. 209,835, filed Nov. 24, 1980, now abandoned.

BACKGROUND AND PRIOR ART

A first report that milk contains a substance capable of reducing cholesterol blood levels appeared in 1974. Mann, G. V. and A. Spoerry, Studies of Cholesteremia in the Maasai, *American Journal Clinical Nutrition*, 27, 464 (1974). This report was based on a feeding trial with Maasai male adults in Kenya. The objective of the test was to determine the effect on cholesterol levels of the addition to Maasai milk of an emulcent food additive (Tween) which had been shown to cause a cholesterol rise in rabbits. No significant effect was found from the food additive, but analysis of the data showed that the more milk consumed the lower the level of cholesteremia observed in the men. Subsequent feeding trials which were conducted with milk and yogurt by Dr. George V. Mann and his associates, using rats, rabbits, and human subjects, confirming the observation that milk contains a substance which lowers the level of cholesterol. As named by Dr. Mann, this substance is now called Milk Factor or MF. See Nair, C. R. and G. V. Mann, *Atherosclerosis*, 26, 335 (1977); and Mann G. V., *Atherosclerosis*, 26, 335 (1977); and Mann, G. V., *Atherosclerosis*, 27, 383 (1977). The existence of Milk Factor and it's action in reducing blood cholesterol levels is mammals is now well established, having been confirmed by several other investigators. These literature reports include: Howard, A. N. and J. Marks, *Lancet*, 2, 255 (1977); Malinow, M. R. and P. McLaughlin, *Experientia*, 31, 1012 (1975); Kritchevsky, D., S. A. Tepper et al, *American Journal Clinical Nutrition*, 31, 518 (1978); and Hepner, G., R. Fried et al, *American Journal Clinical Nutrition*, 32, 19 (1979).

The research on which the present application is based has been partially published: Mann, G. V., Milk Factor—A Regulator of Cholesteremia, *Abstract American Society of Clinical Nutrition*, (May 3, 1979); and Mann, G. V., Ein Regulator den Cholesteramie, *Bulletin European Organization for Control of Circulatory Disease*, (Bonn, Nov. 9, 1979). As reported in the cited abstract, Dr. George V. Mann discovered a variety of *Pseudomonas fluorescens* which when propagated in milk was capable of producing from a 25 to 50 fold increase in the Milk Factor content of the milk. This microorganism is also referred to with respect to its MF-producing capacity in the cited Bulletin, although not further identified therein. Milk Factor itself was described as a small, non-protein, acidic, volatile molecule, which had not yet been molecularly characterized. The new strain or sub-species of *P. fluorescens* discovered by Dr. Mann has not been publicly available, and has been maintained under the control of Dr. Mann in his laboratory at Vanderbilt University School of Medicine, Department of Biochemistry, Nashville, Tenn. In connection with the filing of the prior application, Ser. No. 209,835, this strain or sub-species was deposited on a restricted basis with the American Type Culture Collection, Rockville, Md., and has been assigned the name *Pseudomonas fluorescens loitokitok* (ATCC No. 31732).

DESCRIPTION OF PREFERRED EMBODIMENTS

In one of its aspects, this invention relates to a method of producing Milk Factor (MF) in which *Pseudomonas fluorescens loitokitok* or an MF-producing strain derived therefrom is propagated to obtain a culture for use as an inoculant. The culture is then employed to inoculate a liquid medium containing milk as the principal constituent. The culture is propagated in the medium with concomitant production of MF therein. The new strain of *P. fluorescens*, which is employed in practicing the present invention, was obtained from a sample of cultured Maasai milk collected near the village of Loitokitok, Kenya. Other samples of cultured Massai milk similarly collected were not found to contain this strain or similar MF-producing strain. Cultures of the original isolate have been placed on deposit with the American Type Culture Collection, Rockville, Md., and are now further identified by ATCC No. 31732.

Taxonomy

Using standard classification tests, it was determined that *Pseudomonas fluorescens loitokitok* was classifiable as *Pseudomonas fluorescens* Biotype I (Stanier's Group A). See, Stanier, R. Y., et al, The Aerobic Pseudomonads: A Taxonomic Study, *Journal General Microbiology*, 43, 159 (1966); and *Bergey's Manual of Determinative Bacteriology*, Eighth Edition, Williams and Wilkens, Baltimore, Md. (1978). Based on presently available evidence, *Pseudomonas fluorescens loitokitok* has the unique characteristic of producing Milk Factor in high yield when propagated in milk. This property is therefore an important characteristic for the purpose of the present invention. It appears that *Pseudomonas fluorescens loitokitok* can exist in two colony types, one of which metabolizes carbon sources at a slower rate than the other. Either or both of these colony types can be used for the purposes of the present invention.

*Pseudomonas fluorescens loitokitok* (hereinafter referred to as "PFL") may be preserved by freeze-drying, or in a liquid nitrogen frozen culture. On rehydration or thawing, the viable cells may be propagated in standard culture media. For example, the PFL cells may be propagated in trypsinized soy broth (TSB). Suitable standard media used by the American Type Culture Collection are designated as Medium 3 and Medium 26. A propagation temperature of 30° C. is suitable, and air or oxygen should be present. Using TSB or similar standard non-milk medium, cultures of PFL can be produced for use as an inoculant in practicing the present invention. With media which do not contain milk, PFL elaborates smaller amounts of MF, but good cell growth occurs. If desired, the inoculant culture may be produced by using a media containing milk or milk protein.

PFL cultures for use as inoculant cultures typically is a 48 hour growth of the organism in TSB. Cultures containing higher or lower cell counts can also be used. A suitable inoculant level for propagating PFL to produce Milk Factor is about 1% of the TSB culture medium added to sterile whole milk. A particularly advantageous medium is whole milk, which may be homogenized and sterilized by a suitable procedure such as autoclaving. Unhomogenized pasteurized whole milk may also be used, as well as skim milk which may be either sterilized or pasteurized. There appears to be an advantage, to employing a media containing milk fat because the presence of milk lipids appears to enhance the production of MF. More generally, however, the PFL culture may be propagated for MF production in any medium containing milk or milk protein as the principal constituent thereof. The milk protein may be provided by reconstituted nonfat dry milk (NFDM) or from whey protein, as well as from fresh milk.

Instead of the preferred PFL culture, as described above, other Milk Factor-producing strains of *Pseudomonas fluorescens* can be employed. It appears that many strains of *P. fluorescens* produce significant amounts of Milk Factor. Suitable strains are available from the American Type Culture Collection, Rockville, Md. Publicly available strains capable of producing Milk Factor in substantial yields are further identified by ATCC Nos. 17397, 17570, 17554, 17557, 17563, 17564, 17565, 17568, and 17569. These strains may be propagated to produce suitable inoculant cultures for use in the fermentation process of the present invention, using the procedures described above for the PFL culture.

The fermentation for production of MF can be carried out at a temperature of from 23° to 37° C. However, a temperature of around 30° C. is optimal. No pH adjustment of the medium is required either before or during fermentation, the normal pH of milk being satisfactory (around pH6.8). The organism does not produce acid.

The fermentation is preferably continued until a maximum yield of MF is obtained. Usually, a maximum yield is obtained in about 4 to 8 days. However, longer or shorter fermentation times can be used. The progress of the MF production may be followed by using an MF assay procedure, as will be subsequently described herein. In this assay, a rat liver homogenate is supplied to radio-acetyl CoA substrate. One MF unit is defined as the activity which will inhibit synthesis of cholesterol in this system by one percent. By this assay, the Milk Factor content in samples of whole milk, skim milk, and yogurt was determined and compared with the MF content of whole milk fermented with PFL, as described above. The comparison is summarized on the following page in Table A.

TABLE A

| Substrate | Mf Units/ml |
|---|---|
| Whole Milk | 4,800 |
| Skim Milk | 5,200 |
| Yogurt | 7,000 |
| PPL-fermented whole milk (7 day) | 75,000 |

It has been further discovered that the production of MF can be enhanced by the presence of a small amount of glutaconic acid or a water-soluble salt thereof in the fermentation medium. Glutaconic acid is commercially available in its trans form, which is suitable for use in the present invention. Glutaconic acid at a pH such as 6.8, exists as a salt in aqueous solution, such as in sodium, potassium, or calcium salt. Therefore, when these ions are present in the medium, as they will be when employing media containing milk or milk protein, the glutaconic acid which is added in that form will be present in the fermentation media, in effect, as glutaconate. Alternatively, therefore, if available, it may be added in that form, such as in the form of the sodium or potassium salts of glutaconic acid. It is the presence of the glutaconate anion which is important for enhancing the yield of the MF. The amount employed can range from as little as 0.1 to as much as 10.0 millimiles (mM) of glutaconic acid or glutaconate per liter of medium. A preferred level is from 1.0 to 5.0 mM per liter. The results obtainable by the use of this additive are indicated by the comparative data set out on the next page in Table B.

TABLE B

| Fermentation Time (days) | nM Glutaconate/l. Milk Medium[1] | | | | | |
|---|---|---|---|---|---|---|
| | 0 | 0.1 | 0.5 | 1.0 | 2.0 | 5.0 |
| 0 | 5000[2] | 5000 | 5000 | 5000 | 5000 | 5000 |
| 2 | 12000 | 13000 | 14000 | 14000 | 14000 | 15000 |
| 4 | 22500 | 32500 | 41000 | 63000 | 60000 | 58000 |
| 6 | 39500 | 53000 | 71000 | 125000 | 130000 | 105000 |
| 8 | 42000 | 36500 | 46000 | 35000 | 36000 | 35000 |
| 10 | 40000 | 24000 | 30000 | 31000 | 32000 | 30000 |

[1] Whole homogenized sterilized milk inoculated with PFL and fermented at 30° C.
[2] MF units/ml. medium As will be apparent from the foregoing data, the method of this invention can be employed to enhance the Milk Factor content of milk by from 10 to 25 fold. The milk containing the enhanced MF can be used as a beverage, preferably after sterilization or pasteurization, or converted into a milk product such as yogurt, cheese, or ice cream. The pH of the milk does not appreciably change during the fermentation, the final pH approximating the starting pH (viz., pH6.8).

The method of this invention may also be employed for preparing a concentrate of Milk Factor for manufacturing purposes. For example, after the culture has been propagated in a suitable media containing milk or milk protein as the principal component, and preferably also glutaconic acid/glutaconate as previously described, the resulting fermentation medium containing the elaborated milk factor is further processed, and the MF is recovered and concentrated. For example, the residual milk protein may be precipitated and removed from the medium, and part or all of the lactose may also be precipitated and removed. A methanol/acetone cold-precipitation at pH3.0 may be used for this purpose. After filtering to remove the precipitate, a clear solution will be obtained, which can be evaporated to dryness for recovery of the solids containing the Milk Factor. Where the acidity of the medium has been adjusted to an acid pH, such as a pH of from 3.0 to 4.0, as a preliminary to the methanol/acetone precipitation, it is preferred to readjust the pH to near neutrality before removal of the solvents. For example, the medium can be neutralized (pH6.5) by adding ammonium hydroxide, and the solids recovered by evaporation under reduced pressure at a temperature of from 35° to 45° C.

The solid residue containing the MF will also contain some milk lipids if present in the fermentation medium as preferred. The milk fat can be extracted from the neutral solids with a suitable organic solvent extraction, such as with ethyl ether. The lipid extract will be discarded and the remaining solids may be further processed for preparing the MF concentrate. The MF, which may be present as its ammonium salt, is soluble in the lower alcohols, such as methanol or ethanol. The residue from the lipid extraction may therefore be further processed by extraction with methanol or ethanol, which is preferably acidified with hydrochloric acid, such as 1% HCl in the alcohol. Repeated extractions may be made, clarified by filtration, and combined to obtain the MF extract. This extract may then be further concentrated by evaporation of the alcohol. By this procedure, for example, the MF may be concentrated to a volume of 1% or less of the starting fermentation medium. Such concentrates can contain from $1 \times 10^6$ to $1 \times 10^7$ MF Units per milliliter. Such concentrates may be further processed, if desired, to recover the MF in solid form, either amorphus or crystalline.

Presently preferred embodiments of the present invention and of the assay procedure for use in connection therewith are further illustrated by the following examples.

EXAMPLE I 250 ml of whole, pasteurized milk is autoclaved at 15 lbs/in. for 15 minutes in a culture flask. A sterile solution of "trans" glutaconic acid in water is added to supply a final concentration of 2 mM/l of glutaconate.

The media is seeded with 2.5 ml of a 48-hour culture of *Pseudomonas fluorescens loitokitok* (ATCC No. 31732) and incubated for 7 days at 30° C. in air.

The pH of the mixture is adjusted to 3.5 with concentrated HCL and 2250 ml of methanol (9 volume) is added. The mixture is cooled to 5° C. with 2500 ml (10 volume) of reagent grade acetone is added. After 12 hours at 5° the solids are removed by filtration with Celite on a Buchner funnel.

The amber filtrate is adjusted to pH6.50 with concentrated NH4OH and filtered again. The clear filtrate is reduced to dryness, 40° C. in a vacuum rotary. The brown residue is extracted once with ethyl ether at 35° C. and the extract is discarded. The residue is extracted repeatedly with small volumes of boiling methanol containing 1% HCL. The extracts are pooled through a paper filter. The final volume is adjusted to 25 ml. This should contain about $1 \times 10^6$ units of MF.

EXAMPLE II

The assay for MF is a modification of the procedure described by Goodwin and Margolis-JBC-248, 7610 (1973).

| Buffer | mM |
|---|---|
| Hepes | 275 (pH 7.2) |
| K2HPO4 | 10 |
| nicotinamide | 39 |
| EDTA | 2 |
| MgCl2 | 4 |

| Co-Factors | Concentration |
|---|---|
| 3H AcetylcoA | .038 mM containing 0.1 uci 3H |
| ATP | 1 mM |
| NADP | .5 mM |
| G6Phosphate | 3.0 mM |

Procedure:

In the morning a young rat between 3 and 4 weeks old and preferably weighing less than 65 g. is decapitated and allowed to bleed. The liver is removed to a beaker of cold normal saline. Three grams of liver is transferred to a cold beaker and 27 ml of the buffer is added. The mixture is ground in a Potter-Elvejhem mortar on a mechanical stirrer with two complete plunges to the bottom of the pestle. The homogenate is transferred to a centrifuge cup and spun for 10 minutes at 600 g. at 5° C. The supernatant is decanted to a small cold flask.

The samples are prepared by distributing appropriate amounts of material to a row of $15 \times 125$ millimeter screw-cap tubes. If solvent is present this is removed in vacuo at 65° C. The volumes are adjusted to 100 μl with buffer.

The liver homogenate is then distributed, 300 microliters to each assay tube held in a bath at 37° C. The liver is incubated with shaking at a rate of 125 oscillations per minute for 25 minutes. 100 microliters of co-factor is then added to each tube and after 30 minutes of pre-incubation 50 μl of the $3_{HACoA}$ is added to each tube. This supplies a final concentration of 0.038 micromoles and approximately 0.1 microcurie per assay.

The tubes are shaken for 30 minutes at 37°. The reaction is stopped by adding 5 ml of 0.4 M KOH in ethanol. The tubes are mixed and heated for 1 hour at 65°. To each tube is added 5 ml of water followed by exactly 5 ml of petroleum ether. The tubes are capped and shaken vigorously. After the petroleum ether layer has separated, exactly 4 ml is removed to a centrifuge tube and taken to dryness in a vacuum oven at 65° C.

To each tube is added one drop of 5% hydrochloric acid and 1 ml of a carrier solution of cholesterol containing 300 micrograms of re-crystallization cholesterol in 1 ml of 2-1 acetone-alcohol. To each tube is added 1 ml of a digitonin solution containing 0.5 percent digitonin in 50 percent ethanol. The tubes contents are mixed and allowed to stand at room temperature for 2 hours. The digitonide is spun down at 5° C., the supernatant is discarded, and the digitonide is washed once with 2-1 acetone-ether and then with ethyl ether. The digitonide is dissolved in 0.5 ml of methanol and the entire solution is transferred to a scintillation bottle. An organic scintillation fluid is added and the tubes are counted in a scintillation spectrometer.

With each sample assayed are duplicate control tubes, that is without sample present. Four pairs of sample tubes are selected to bracket the 50% inhibition point. The calculation is done by substracting the background and calculating the percent of the control tubes observed in each pair of sample tubes. The microliters of original sample necessary to produce a 50% inhibition of the incorporation of acetylcoA into cholesterol is then determined graphically and this is used to calculate the units of MF per milliliter of original sample. Thus, $$\frac{50 \times 1000}{I_{50\ \mu l}} = \text{units/ml}$$

where 1 unit is the amount of inhibitory activity which will suppress the incorporation of acetylcoA into cholesterol by 1%.

The inhibition curve when plotted is typically a negative parabola. Sample volumes which do not bracket the 50% inhibition point are re-assayed with more appropriate sample sizes or dilutions. Typically an assay system uses 5, 10, 20, 40, microliter sample sizes. With these conditions an ordinary sample of pasteurized whole milk will give an $I_{50}$ of about 10 microliters which calculates to 5,000 units of MF per milliliter of original milk.

I claim:

1. The method of producing Milk Factor (MF), comprising:
    (a) propagating an MF-producing strain of *Pseudomonas fluorescens* to obtain a culture thereof for use as an inoculant;
    (b) inoculating an aqueous culture medium with said culture, said medium containing milk or milk protein as the principal constituent thereof and also containing an effective amount of glutaconic acid or a soluble salt thereof for enhancing the production of MF in said medium; and (c) propagating said culture in said medium with concomitant production of MF therein.

2. The method of claim 1 in which said culture is propagated from cells of the strain deposited under ATCC No. 31732.

3. The method of claim 1 or claim 2 in which said medium contains from 1.0 to 5.0 millimoles (mM) per liter of glutaconic acid or a soluble salt thereof.

4. The method of claim 1 or claim 2 in which said medium is whole milk.

5. The method of producing Milk Factor (MF) comprising:

(a) propagating cells of an MF-producing strain of *Pseudomonas fluorescens* to obtain a culture thereof for use as an inoculant;

(b) inoculating an aqueous culture medium with said culture, said medium also containing from 1.0 to 5.0 millimoles (mM) per liter of trans glutaconic acid or water-soluble salt thereof;

(c) propagating said culture in said medium with production of Milk Factor; and (d) recovering and concentrating said Milk Factor.

6. The method of claim 5 in which said medium is whole milk.

7. The Milk Factor concentrate produced by the method of claim 5 or claim 6.

* * * * *